(12) United States Patent
Kuebler et al.

(10) Patent No.: US 10,722,619 B2
(45) Date of Patent: Jul. 28, 2020

(54) METHOD FOR OPERATING AN OPHTHALMOSURGICAL SYSTEM

(71) Applicant: Carl Zeiss Meditec AG, Jena (DE)

(72) Inventors: Christoph Kuebler, Oberkochen (DE); Friederike Neis, Ulm (DE); Nadine Geller, Koenigsbronn (DE); Melanie Schuch, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 130 days.

(21) Appl. No.: 16/173,738

(22) Filed: Oct. 29, 2018

(65) Prior Publication Data

US 2019/0060533 A1    Feb. 28, 2019

Related U.S. Application Data

(63) Continuation-in-part of application No. 15/419,771, filed on Jan. 30, 2017, now Pat. No. 10,639,196.

(30) Foreign Application Priority Data

Jan. 28, 2016    (DE) .......................... 10 2016 201 297

(51) Int. Cl.
*A61M 1/00*    (2006.01)
*A61F 9/007*    (2006.01)

(52) U.S. Cl.
CPC ....... *A61M 1/0031* (2013.01); *A61F 9/00745* (2013.01); *A61M 1/0058* (2013.01);
(Continued)

(58) Field of Classification Search
CPC .............. A61M 1/0058; A61M 1/0037; A61M 1/0066; A61M 3/0258; A61M 3/0216;
(Continued)

(56) References Cited

U.S. PATENT DOCUMENTS 5,261,883 A    11/1993  Hood et al.
6,267,752 B1 *  7/2001  Svetliza ............... A61B 3/0008
                                               600/205
(Continued)

FOREIGN PATENT DOCUMENTS

JP    H01-151455 A    6/1989
JP    H05-115502 A    5/1993
(Continued)

OTHER PUBLICATIONS

English translation and Office action of the Japanese Patent Office dated Nov. 5, 2019 in corresponding Japanese patent application JP 2018-188860.

(Continued)

*Primary Examiner* — Manuel A Mendez
*Assistant Examiner* — Tasnim Mehjabin Ahmed
(74) *Attorney, Agent, or Firm* — Walter Ottesen, P.A.

(57) ABSTRACT

The invention is directed to a method of operating an ophthalmosurgical system which includes a console for accommodating an irrigation fluid vessel containing irrigation fluid and a cassette, insertable into the console, for directing the irrigation fluid to a surgical instrument for an eye to be treated. An irrigation fluid flow path leads from the irrigation fluid vessel to the cassette and to the surgical instrument. A first fluid pump includes a first pump chamber having a first volume and a first drive chamber separated therefrom by a first elastic partition and having a second volume. A second fluid pump is arranged in parallel to the first fluid pump and includes a second pump chamber having a third volume and a second drive chamber separated therefrom by a second elastic partition and having a fourth volume.

2 Claims, 4 Drawing Sheets

(52) U.S. Cl.
CPC ..... *A61M 1/0066* (2013.01); *A61B 2217/005* (2013.01); *A61B 2217/007* (2013.01); *A61F 9/007* (2013.01); *A61F 9/00781* (2013.01); *A61M 1/008* (2013.01); *A61M 2205/12* (2013.01); *A61M 2205/3337* (2013.01); *A61M 2205/3379* (2013.01); *A61M 2210/0612* (2013.01)

(58) Field of Classification Search
CPC . A61M 3/0283; A61B 2217/005; A61F 9/007
See application file for complete search history.

(56) References Cited

U.S. PATENT DOCUMENTS

| | | |
|---|---|---|
| 2006/0135974 A1 | 6/2006 | Perkins |
| 2007/0083150 A1 | 4/2007 | Nazarifar et al. |
| 2012/0215160 A1 | 8/2012 | Valenti et al. |
| 2015/0164690 A1* | 6/2015 | Peterson ............. A61F 9/00736 604/67 |
| 2015/0196425 A1 | 7/2015 | Kuebler et al. |
| 2015/0297405 A1* | 10/2015 | Bourne ............... A61F 9/00736 604/31 |
| 2015/0328379 A1 | 11/2015 | Carr et al. |
| 2017/0216093 A1 | 8/2017 | Kuebler et al. |

FOREIGN PATENT DOCUMENTS

| | | |
|---|---|---|
| JP | 2002-153499 A | 5/2002 |
| JP | 2008-523959 A | 7/2008 |
| JP | 2014507972 A | 4/2014 |
| JP | 20140064934 A | 4/2014 |
| WO | 9318802 A1 | 9/1993 |
| WO | 2015/161149 A1 | 10/2015 |

OTHER PUBLICATIONS

English translation of the Office action of the Japanese Patent Office dated May 18, 2018 in corresponding Japanese patent application JP 2017-008276.

English translation and Office action of the German Patent Office dated Nov. 11, 2016 in German patent application 10 2016 201 297.5 on which the claim of priority is based.

English translation and Office action of the Japanese Patent Office dated Oct. 1, 2019 in corresponding Japanese patent application JP 2018-188859.

* cited by examiner

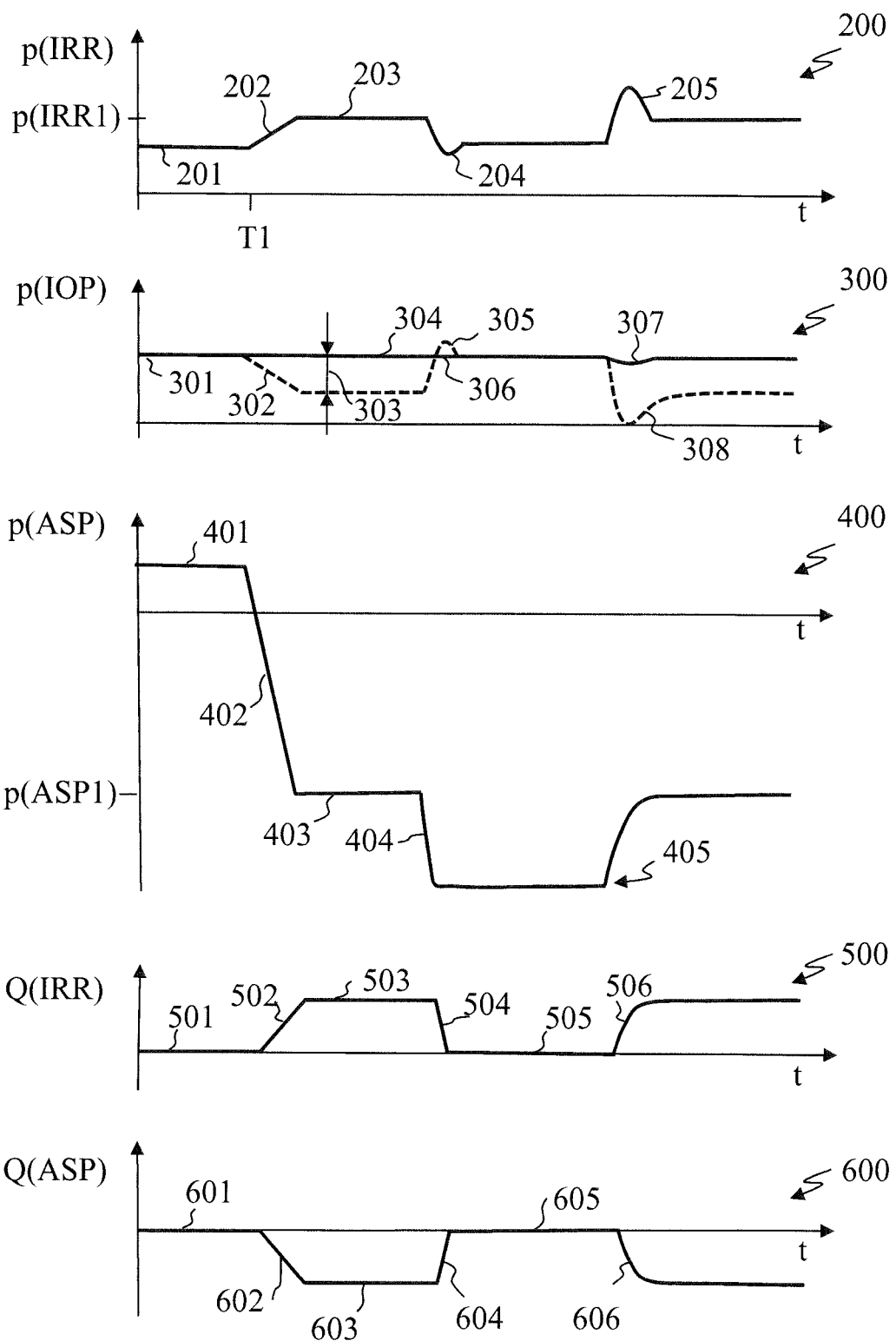

METHOD FOR OPERATING AN OPHTHALMOSURGICAL SYSTEM

CROSS REFERENCE TO RELATED APPLICATIONS

This application is a continuation-in-part application of U.S. patent application Ser. No. 15/419,771, filed Jan. 30, 2017 which, in turn, claims priority of German patent application no. 10 2016 201 297.5, filed Jan. 28, 2016, and the entire contents of both applications are incorporated herein by reference.

FIELD OF THE INVENTION

The invention is directed to a method for operating an ophthalmosurgical system.

BACKGROUND OF THE INVENTION

There are multiple surgical techniques for treating a clouding of the lens, which is referred to as a cataract in medicine. The most widespread technique is phacoemulsification, in which a thin hollow needle is introduced into the eye lens and induced to make ultrasonic vibrations. In its immediate surroundings, the vibrating hollow needle emulsifies the lens such that the resulting lens particles can be aspirated through a line by a pump. A flushing fluid (irrigation fluid) is fed during this process, with the aspiration of the lens particles and of the fluid taking place through an aspiration line. When the lens has been completely emulsified and removed, a new artificial lens can be inserted into the empty capsular bag, and so a patient treated in this way can reattain good vision.

During fragmentation of the eye lens by a hollow needle vibrating with ultrasound, it is not possible to avoid a relatively large lens particle reaching the tip of the hollow needle during the surgical procedure such that the needle tip or its aspiration opening becomes clogged. This state is referred to as occlusion. In such a case, a peristaltic pump typically used in the aspiration line builds up a suction pressure which is much stronger in comparison with an occlusion-free operation. In addition, a high energy input for movement of the hollow needle can be effected, so that the lens particle clogging the hollow needle is broken to pieces. Alternatively, a reversal of the direction of movement of the peristaltic pump can also remove the lens particle from the needle tip, and so a normal aspiration of the fluid and of the small lens particles can proceed again. In such a moment, an occlusion is therefore broken up, with the previously present high negative pressure decreasing very rapidly. The resulting suction can lead to not only small lens particles and fluid being drawn to the aspiration line, but also part of the capsular bag coming into contact with the hollow needle. If the capsular bag is punctured, this leads to considerable complications for the patient, which complications must be absolutely avoided. Moreover, during the suction, a large quantity of fluid can be aspirated from the anterior chamber of the eye, and so there is the risk of the eye collapsing. This too can lead to considerable complications for the patient, which complications must be absolutely avoided.

Further systems for steering a fluid are described in United States patent application publication 2015/0164690 A1, WO 93/18802 A1 and United States patent application publication 2015/0297405 A1.

SUMMARY OF THE INVENTION

It is an object of the invention to provide a method of operating an ophthalmosurgical system which keeps the intraocular pressure to a low value of less than 50 mm Hg over the entire period of a surgical procedure. It is intended that the intraocular pressure be kept virtually constant during the surgical procedure, with this also being achieved at the start of and after breakup of an occlusion. It is intended that this be possible during a short surgical procedure and during a long surgical procedure. Furthermore, it is intended that the system be cost-effective.

The ophthalmosurgical system according to the invention comprises:

a console for accommodating an irrigation fluid vessel containing irrigation fluid;

a cassette, insertable into the console, for steering the irrigation fluid to a surgical instrument for an eye to be treated;

an irrigation fluid flow path from the irrigation fluid vessel to the cassette and to the surgical instrument;

a first fluid pump which comprises a first pump chamber having a first volume and a first drive chamber separated therefrom by a first elastic partition element and having a second volume, wherein the first elastic partition element is permanently mounted by its edge in the first fluid pump;

wherein irrigation fluid from the irrigation fluid flow path is feedable to the first pump chamber and a first drive fluid, by which it is possible to achieve an elastic deformation of the first elastic partition element, is feedable to the first drive chamber on the basis of a predetermined pressure, and, as a result, the first volume can be made smaller and, at the same time, the second volume can be made larger;

a second fluid pump which is arranged in parallel to the first fluid pump and which comprises a second pump chamber having a third volume and a second drive chamber separated therefrom by a second elastic partition element and having a fourth volume; wherein the second elastic partition element is permanently mounted by its edge in the second fluid pump, wherein irrigation fluid from the irrigation fluid flow path is feedable to the second pump chamber and a second drive fluid, by which it is possible to achieve an elastic deformation of the second elastic partition element, is feedable to the second drive chamber on the basis of a predetermined pressure, and, as a result, the third volume can be made smaller and, at the same time, the fourth volume can be made larger;

wherein the first volume or the third volume has a size within the range from 1 to 25 cm$^3$.

The system therefore comprises a first fluid pump and a second fluid pump connected in parallel thereto. For example, when, in the case of the first pump, the first pump chamber is almost empty, the second fluid pump can be connected. When the second fluid pump, with its second pump chamber, is releasing irrigation fluid into the irrigation fluid flow path, the first fluid pump can be refilled, and so, after emptying of the second pump chamber, the first fluid pump can be connected again. This means that an alternating activation of the first fluid pump and of the second fluid pump is possible. This makes it possible to achieve a volume flow with very low fluctuations during a surgical procedure. This means that a virtually constant intraocular pressure is attainable. The alternating activation of the first and second fluid pumps connected in parallel can take place until there is no more irrigation fluid present in the irrigation fluid vessel. This means that it is possible to operate the system during a short surgical procedure and during a very long surgical procedure without interruption of the flow of irrigation fluid.

The fluid pumps each comprise an elastic partition element which is permanently mounted by its edge in the particular fluid pump. A movement of the elastic partition element is achieved by a drive fluid, which is provided in an associated drive chamber of the particular fluid pump. The elastic partition element is therefore not moved by a plunger or a rod, as is the case for a piston, but by a drive fluid. This allows a jerk-free and very rapid movement, for example, without initial sticking with subsequent slipping as in the case of a piston (also known as the "stick-slip effect"). Such an elastic partition element can also be made with a small mass, which element allows a dynamic movement and thus a dynamic fluid change in the irrigation fluid flow path. Since the elastic partition element is attached at the edge of the particular fluid pump, it is possible to achieve a good seal. A movement of the elastic partition element at the edge of the fluid pump therefore does not occur. Therefore, it is possible to omit a lubricant for a good slip, as would be necessary in the case of a piston pump. This is particularly advantageous, since, in the system according to the invention, there is therefore no risk of the irrigation fluid being contaminated. On the contrary, it is ensured that the irrigation fluid can remain sterile during activation of the fluid pumps. In addition, the good sealing effect due to an elastic partition element makes it possible to use any desired drive fluid. It is conceivable for the fluid to likewise be irrigation fluid. However, it is also possible for compressed air from a stationary compressed air line to be involved. The good sealing effect due to an elastic partition element ensures that there is no contact between irrigation fluid of the pump chamber and drive fluid of the drive chamber.

The first volume of the first pump chamber or the third volume of the third pump chamber has a size within the range from 1 to 25 $cm^3$, preferably a size within the range from 1 to 15 $cm^3$ and particularly preferably a size within the range from 1 to 10 $cm^3$. This represents a relatively small volume. Owing to the possibility of providing an alternating operation of the fluid pump, a long surgical procedure is, however, possible without interruption. Moreover, a small first and third volume is advantageous, since a relatively small change in the volume flow in the irrigation fluid flow path brings about a proportionally relatively large change in the first and third volume. This means a relatively high sensitivity in the detecting of a change in volume flow. Furthermore, a small first volume and/or third volume means that only small masses are to be conveyed, and so the system can be altogether made small and compact and thus implemented cost-effectively.

Preferably, the first volume has the same size as the third volume. This makes it possible to achieve a symmetrical construction with virtually the same switching frequencies of the associated valves.

According to one embodiment, the system according to the invention additionally comprises the following:

an aspiration fluid flow path for feeding aspiration fluid from the eye to be treated to an aspiration fluid collection vessel, a third fluid pump which comprises a third pump chamber having a fifth volume and a third drive chamber separated therefrom by a third elastic partition element and having a sixth volume, wherein the third elastic partition element is permanently mounted by its edge in the third fluid pump, wherein aspiration fluid from the aspiration fluid flow path is feedable to the third pump chamber and a third drive fluid, by which it is possible to achieve an elastic deformation of the third elastic partition element, is feedable to the third drive chamber on the basis of a predetermined pressure, and, as a result, the fifth volume can be made larger and, at the same time, the sixth volume can be made smaller, a fourth fluid pump which is arranged in parallel to the third fluid pump and which comprises a fourth pump chamber having a seventh volume and a fourth drive chamber separated therefrom by a fourth elastic partition element and having an eighth volume, wherein the fourth elastic partition element is permanently mounted by its edge in the fourth fluid pump, wherein aspiration fluid from the aspiration fluid flow path is feedable to the fourth pump chamber and a fourth drive fluid, by which it is possible to achieve an elastic deformation of the fourth elastic partition element, is feedable to the fourth drive chamber on the basis of a predetermined pressure, and, as a result, the seventh volume can be made larger and, at the same time, the eighth volume can be made smaller, wherein the fifth volume or the seventh volume has a size within the range from 1 to 25 $cm^3$.

In the aspiration fluid flow path, a construction similar to the irrigation fluid flow path is therefore provided. A third fluid pump is arranged in parallel to a fourth fluid pump in order to pump out aspiration fluid from the eye to an aspiration fluid collection vessel. The pumps are operable in an alternating manner and each comprise an elastic partition element, making possible a tight partition between a particular pump chamber and an associated drive chamber. Owing to the relatively small fifth volume or seventh volume which has a size within the range from 1 to 25 $cm^3$, preferably a size within the range from 1 to 15 $cm^3$ and particularly preferably a size within the range from 1 to 10 $cm^3$, a rapid and dynamic response to a change in pressure in the aspiration line is possible. When, for example, a needle of the surgical instrument is clogged or occluded with a lens particle, no more aspiration fluid flows into the aspiration fluid flow path. After breakup of the clogging, this state changes very rapidly, by fluid being aspirated from the eye in an almost sudden manner. Once this is identified, this change can be handled effectively by a very dynamically operable third and fourth fluid pump, making it possible to achieve a virtually constant intraocular pressure.

A further advantage of this embodiment is that an aspiration without pulsation is possible over the entire period of a surgical procedure. This represents a distinct improvement in comparison with systems which convey the aspiration fluid by a peristaltic pump. An operation without pulsation is advantageous, since the eye to be treated can therefore lie still over the entire duration of the surgical procedure and a steady image is presented to a surgeon when observing through a microscope.

Preferably, the fifth volume has the same size as the seventh volume. This makes it possible to achieve a symmetrical construction with virtually the same switching frequencies of the associated valves.

According to a further embodiment, a particular position of the first elastic partition element and of the second elastic partition element is detectable in a contactless manner by a respective first and second sensor. Knowledge of the position of the first and second elastic partition element allows an indirect establishment of the volume flow in the irrigation fluid flow path. Therefore, it is possible by the first and second drive fluid to directly influence the volume flow in the irrigation fluid flow path. This is particularly important when a breakthrough of an occlusion occurs and a rapid and dynamic change in the irrigation fluid volume flow is required in order to achieve a virtually constant intraocular pressure.

A further advantage is that, in the case of such an indirect establishment of the volume flow, air bubbles in the irrigation fluid are insignificant. In a pressure measurement or volume flow measurement, as are customary in ophthalmosurgical systems according to the prior art, air bubbles, especially foam, have, however, a highly interfering effect on the measurement result and can greatly distort it. Thus, when air bubbles in the irrigation fluid cannot be avoided, it is nevertheless possible according to the embodiment to achieve a precise regulation of the volume flow in the irrigation fluid flow path and thus a regulation of the subsequently ensuing pressure in the eye.

A further possibility is that the particular position of the third elastic partition element and of the fourth elastic partition element is detectable in a contactless manner by a respective third and fourth sensor. This means that the above-described advantages for detecting the position of the first elastic partition element and of the second elastic partition element can be even better achieved. It is therefore also possible, in the aspiration fluid flow path, to indirectly establish the volume flow, making it possible to achieve a rapid and dynamic regulation of the volume flow in the aspiration fluid flow path.

According to a further embodiment, the irrigation fluid is feedable from the first and the second pump chamber at the same time and under a first pressure to the irrigation fluid flow path in the direction of the surgical instrument. When, for example, the first pump chamber is almost empty, it is possible, just before the empty state of the first pump chamber, for irrigation fluid to be fed from the second pump chamber into the irrigation fluid flow path. Since the two pump chambers are connected to one another in parallel, the same pressure is present at the respective outputs of the two pump chambers. Such an embodiment is advantageous, since it is therefore possible to achieve a continuous normal operation of the fed irrigation fluid and, in the case of alternate operation of the pump chambers, no fluctuation of the volume flow and of the pressure in the irrigation fluid flow path occurs.

Furthermore, it is possible for the aspiration fluid to be feedable into the third and into the fourth pump chamber at the same time under a second pressure. This means that the same advantages as in the case of the above-described embodiment are also achievable in the aspiration fluid flow path.

In a further embodiment, the first and second pump chamber for the irrigation fluid and/or the third and fourth pump chamber for the aspiration fluid have in each case an inlet valve and an outlet valve, wherein the particular outlet valve is spatially arranged above the particular inlet valve. This is advantageous, since air bubbles possibly present in the irrigation fluid or aspiration fluid can rapidly escape upward and cannot accumulate in one of the pump chambers in relatively large quantities.

Preferably, the first and the second pump chamber are arranged in the cassette and the first and the second drive chamber are arranged in the console. The first pump chamber having the first volume and the second pump chamber having the third volume each have a relatively small volume, and so the cassette can be small and compact in configuration. Since the cassette is a disposable article, low consumption costs are therefore possible. Such an embodiment of the system according to the invention thus allows a cost-effective operation.

Additionally or alternatively, the third and the fourth pump chamber can be arranged in the cassette and the third and the fourth drive chamber can be arranged in the console. This means that a small and compact construction of the cassette and thus a cost-effective operation is likewise possible.

The invention is also directed to a method for operating the ophthalmosurgical system described above and includes a method for switching of inlet valves and outlet valves for pump chambers of fluid pumps of the ophthalmosurgical system. The method includes the steps of: opening a first outlet valve located in a direction of a flow downstream of an outlet of a first pump chamber arranged adjacently of a first drive chamber and separated therefrom by a first elastic partition element; elastically deforming the first elastic partition element so as to cause an irrigation fluid located inside of the first pump chamber to flow in a third subpath of an irrigation fluid flow path and, from there, to a surgical handpiece, wherein the irrigation fluid has a predetermined irrigation pressure; opening a second inlet valve located in a second subpath of an irrigation fluid flow path in direction of flow upstream of an inlet of a second pump chamber arranged adjacently of a second drive chamber and separated therefrom by a second elastic partition element; elastically deforming the second elastic partition element so as to cause a negative pressure to develop in the second pump chamber so as to cause irrigation fluid to flow from an irrigation fluid vessel along the second subpath and then into the second pump chamber; closing the second inlet valve and increasing the pressure in the second pump chamber until an irrigation pressure occurs therein that is the predetermined irrigation pressure; opening a second outlet valve located in a fourth subpath of an irrigation fluid flow path in a direction of a flow downstream of an outlet of the second pump chamber; elastically deforming the second elastic partition element so as to cause irrigation fluid to flow in the fourth subpath of the irrigation fluid flow path, wherein both the first outlet valve and the second outlet valve are opened so as to permit, with the same predetermined irrigation pressure, irrigation fluid to flow from the third subpath and the fourth subpath to the surgical handpiece; closing the first outlet valve; opening a first inlet valve located in a first subpath of the irrigation fluid flow path in a direction of a flow upstream of an inlet of the first pump chamber; elastically deforming the first elastic partition element so as to cause irrigation fluid to flow in the first pump chamber; closing the first inlet valve and increasing the pressure in the first pump chamber until the predetermined irrigation pressure occurs in the first pump chamber; and, closing the second outlet valve.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
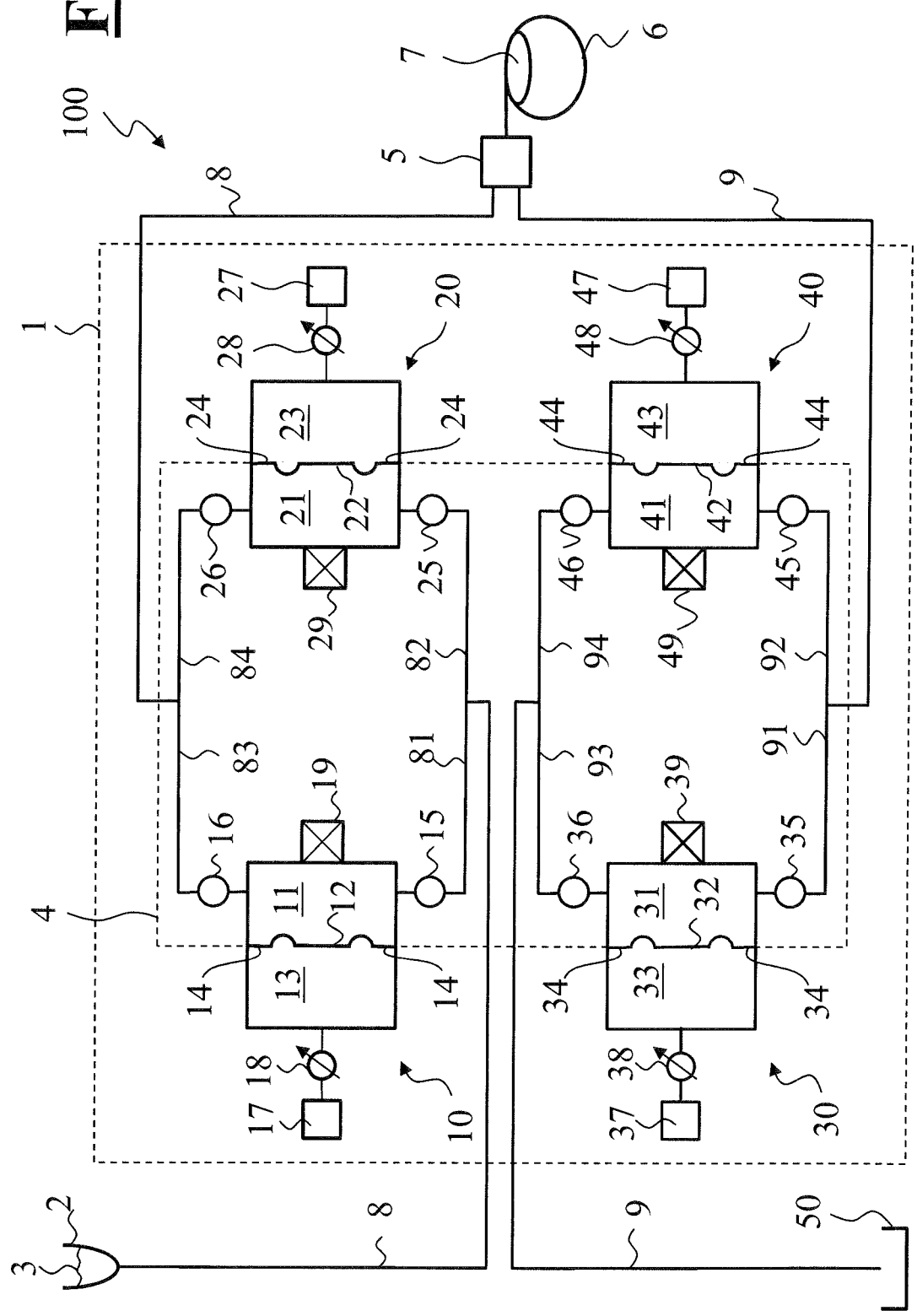
FIG. 1 shows a schematic representation of a first embodiment of the system according to the invention.

FIG. 1 shows a schematic representation of one embodiment of the ophthalmosurgical system 100 according to the invention. The system 100 comprises a console 1, to which an irrigation fluid container or vessel 2 with an irrigation fluid 3 present therein can be coupled. In addition, the system comprises a cassette 4 which is insertable into the console 1. The cassette 4 serves to direct the irrigation fluid 3 to a surgical instrument 5 for an eye to be treated 6. The surgical instrument 5 is suitable for fragmenting a lens 7 of the eye 6, for example by phacoemulsification, it being possible to aspirate the resulting lens particles and the irrigation fluid 3.

The system 100 further comprises an irrigation fluid flow path 8, which runs from the irrigation fluid vessel 2 to the cassette 4 and, from there, to the surgical instrument 5. In addition, the system 100 contains a first fluid pump 10 which comprises a first pump chamber 11 having a first volume and a first drive chamber 13 separated therefrom by a first elastic partition element 12 and having a second volume. The first elastic partition element 12 is permanently mounted at its edge 14 in the fluid pump 10.

The irrigation fluid 3 is feedable to the first pump chamber 11 by the irrigation fluid flow path 8. The irrigation fluid 3 can flow to a first inlet valve 15, reach the first pump chamber 11 when the inlet valve 15 is in the open position, and leave the first pump chamber 11 again in the event of an open outlet valve 16. A first drive fluid 17 can, by a proportional valve 18, be fed to the first drive chamber 13 arranged adjacently to the first pump chamber 11. Depending on a differential pressure between the first drive fluid 17 in the first drive chamber 13 and the irrigation fluid 3 in the first pump chamber 11, there is an elastic deformation of the first elastic partition element 12. When the pressure in the first drive chamber 13 is greater than the pressure in the first pump chamber 11, the first volume of the first pump chamber 11 becomes smaller, and, at the same time, the second volume of the first drive chamber 13 becomes larger. When the inlet valve 15 is closed and the outlet valve 16 is open, irrigation fluid 3 can therefore be conducted out of the first pump chamber 11. The position of the first elastic partition element 12 can be detected by a first sensor 19, which is attached outside the first fluid pump 10. Preferably, the first sensor 19 is an inductive or capacitive position sensor.

The irrigation fluid flow path 8 divides in the cassette 4 into a first subpath 81 and a second subpath 82, which are connected to one another in parallel. The irrigation fluid 3 can therefore also reach the second subpath 82 and, from there, a second fluid pump 20. After passing a second inlet valve 25, it can enter a second pump chamber 21 of the second fluid pump 20 and leave again from the second pump chamber 21 when a second outlet valve 26 is open.

After the first outlet valve 16, the irrigation fluid can flow into a subpath 83, and after the second outlet valve 26, the irrigation fluid can flow into a subpath 84. The subpaths 83 and 84 come together and combine, and so the irrigation fluid flows further only in a single irrigation fluid flow path 8.

Arranged adjacently to the second pump chamber 21, which has a third volume, is a second drive chamber 23, which has a fourth volume, with the second pump chamber 21 and the second drive chamber 23 being separated from one another by a second elastic partition element 22. The second elastic partition element 22 is permanently mounted at its edge 24 in the second fluid pump 20. A second drive fluid 27 can, by a proportional valve 28, be fed to the second drive chamber 23 on the basis of a predetermined pressure.

Depending on the differential pressure between the second pump chamber 21 and the second drive chamber 23, the second elastic partition element 22 arranged therebetween can be elastically deformed. When, for example, the pressure in the second drive chamber 23 is greater than in the second pump chamber 21, the fourth volume of the second drive chamber 23 becomes larger, and, at the same time, the third volume of the second pump chamber 21 becomes smaller. As a result, irrigation fluid 3 can be conducted from the second pump chamber 21 into the subpath 84 of the irrigation fluid flow path 8. The position of the second elastic partition element 22 can be detected by a second sensor 29, preferably in a contactless manner, for example in an inductive or capacitive manner.

When irrigation fluid is guided further by the first fluid pump 10 and/or the second fluid pump 20 into the irrigation fluid flow path 8 after passing the outlet valves 16 and/or 26, the irrigation fluid reaches a surgical instrument 5. The instrument 5 can, for example, be a phacoemulsification handpiece which makes it possible to fragment a lens 7 of an eye 6 into small lens particles.

During the fragmentation of the eye lens 7, the particles are aspirated together with the fed irrigation fluid. According to the invention, this is done by a third fluid pump 30 and a fourth fluid pump 40 connected in parallel thereto. The lens particles and the irrigation fluid contaminated during the fragmentation of the lens, which are together then referred to as aspiration fluid, reach, in the event of an open inlet valve 35, the third fluid pump 30 along an aspiration fluid flow path 9, which divides into a first subpath 91 and a second subpath 92.

The third fluid pump 30 comprises a third pump chamber 31 and a third drive chamber 33 arranged adjacently thereto, which chambers are separated from another by a third elastic partition element 32. The third elastic partition element 32 is permanently joined at its edge 34 to the third fluid pump 30. A third drive fluid 37 can, by a proportional valve 38, be conducted to the third drive chamber 33. When the aspiration fluid flows into the third pump chamber 31 in the event of an open inlet valve 35, the fluid can be conveyed out of the third pump chamber 31 owing to an appropriately high pressure in the third drive chamber 33 and thereby elastically deformed third partition element 32 when the inlet valve 35 is closed and the outlet valve 36 is open. The position of the third elastic partition element 32 can be detected by a third sensor 39. The pumped-out aspiration fluid reaches a subpath 93 and, from there, an aspiration fluid collection container or vessel 50.

These interrelationships also apply analogously to the fourth fluid pump 40. The aspiration fluid can flow along the subpath 92 into a fourth pump chamber 41 having a seventh volume in the event of an open inlet valve 45. Situated adjacently to the fourth pump chamber 41 is a fourth drive chamber 43 having an eighth volume, into which a fourth drive fluid 47 can flow by a proportional valve 48. When the pressure in the fourth drive chamber 43 is greater than in the fourth pump chamber 41, the fourth elastic partition element 42 deforms accordingly, and so the seventh volume becomes smaller and the eighth volume becomes larger. The change in position of the fourth elastic partition element 42 can be detected by a sensor 49. In the event of a closed inlet valve 45 with open outlet valve 46, the aspiration fluid can then flow out of the fourth fluid pump 40 into a subpath 94. The two subpaths 93 and 94 subsequently combine, whereupon the aspiration fluid is conducted to the aspiration fluid collection vessel 50.

The inlet valves 15 and 25 are spatially situated below the outlet valves 16 and 26. This also applies to the inlet valves 35 and 45, which are situated below the outlet valves 36 and 46. This means that it is easily possible to achieve the situation of air bubbles in the irrigation fluid or in the aspiration fluid being rapidly discharged upward and no foam being able to accumulate in a pump chamber.

FIG. 1 is highly schematic, with the pump chambers 10, 20, 30 and 40 being represented with a rectangular cross section. In reality, the pump chambers 10, 20, 30 and 40 can have a round or oval cross section so that the respective elastic partition element 12, 22, 32 and 42 in the event of an elastic deformation can be easily held in position against an inner wall of the corresponding pump chamber 10, 20, 30 and 40 in order to be able to easily push out the fluid contained therein.

The first volume of the first pump chamber 11 preferably has the same size as the third volume of the second pump chamber 21. Also, the fifth volume of the third pump chamber 31 preferably has the same size as the seventh volume of the fourth pump chamber 41.

Figure 2:
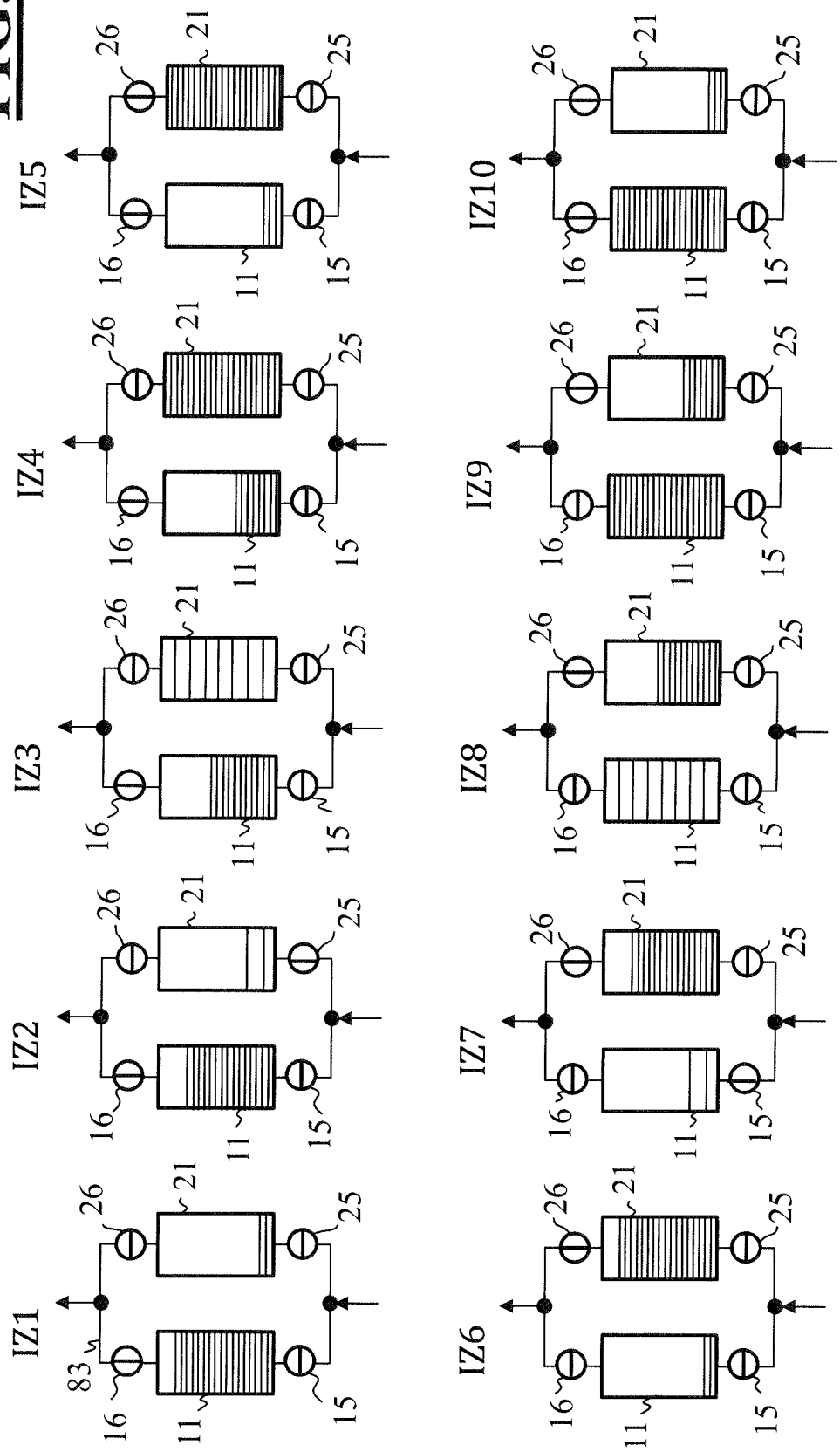
FIG. 2 shows a schematic representation of switching states of inlet and outlet valves of the first and second pump chamber of the system according to the invention.

FIG. 2 shows a schematic representation of switching states of the inlet valve 15 and of the outlet valve 16 for the first pump chamber 11 of the first fluid pump 10 and of switching states of the inlet valve 25 and of the associated outlet valve 26 for the second pump chamber 21 of the second fluid pump 20. The pump chambers 11 and 21 have both been filled with an irrigation fluid. The fill level with the irrigation fluid is indicated by the height of the uppermost shading line of the horizontal shading lines in the particular pump chamber. When the irrigation fluid in the particular pump chamber is contained under a low pressure, the distance between the horizontal shading lines in the particular pump chamber is relatively large. When the irrigation fluid in the particular pump chamber is contained under a high pressure, the distance between the horizontal shading lines in the particular pump chamber is relatively small.

It is assumed that, in a first switching state IZ1, the first pump chamber 11 has been filled with irrigation fluid under a predetermined pressure p(IRR1). The first inlet valve 15 is closed and the first outlet valve 16 is open. In the first drive chamber 13 (not drawn in FIG. 2), there is a predetermined pressure, and so irrigation fluid under a pressure p(IRR1) can flow into the subpath 83 of the irrigation fluid flow path and, from there, to the surgical handpiece. The second pump chamber 21 has only been filled with very little irrigation fluid 3. The second inlet valve 25 is closed; the second outlet valve 26 is similarly closed. In a switching state IZ2, the second inlet valve 25 is opened, and so irrigation fluid can flow from the irrigation fluid vessel 2 into the second pump chamber 21. To this end, the pressure in the second drive chamber 23 is adjusted such that it is lower than the pressure in the second pump chamber 21. A negative pressure therefore arises in the second pump chamber 21 and irrigation fluid is sucked in. When a predetermined quantity of irrigation fluid has flowed in, this being detected by the second sensor 29 on the basis of the position of the elastic partition element 22, the second inlet valve 25 is closed; see switching state IZ3. Subsequently, the pressure in the second drive chamber 23 is increased such that a predetermined irrigation pressure p(IRR1) ensues in the second pump chamber 21; see switching state IZ4. In switching state IZ5, the second outlet valve 26 is opened, and so irrigation fluid under the pressure p(IRR1) can flow into the subpath 84. For a brief interval, which can last 20 milliseconds for example, irrigation fluid under the same pressure p(IRR1) therefore flows in the third subpath 83 and in the fourth subpath 84. During switching states IZ1 to IZ5, the irrigation fluid contained in the first pump chamber 11 flows out.

Subsequently, the first outlet valve 16 is closed—see switching state IZ6—and so no more irrigation fluid can flow from the first pump chamber 11 into the subpath 83. This is done at the moment when the irrigation fluid in the first pump chamber 11 has almost completely flowed out. However, the irrigation fluid continues to flow from the second pump chamber 21 under the pressure p(IRR1) into the subpath 84 of the irrigation flow path and, from there, to the surgical handpiece 5.

In switching state IZ7, the first inlet valve 15 is opened, with a lower pressure being applied in the first drive chamber 13 than in the first pump chamber 11, and so irrigation fluid can flow by suction from the irrigation fluid vessel 2 into the first pump chamber 11. When the first pump chamber 11 contains sufficient irrigation fluid, it being possible to detect this by the first sensor 19 on the basis of the position of the first elastic partition element 12, the first inlet valve 15 is closed in switching state IZ8. Subsequently, in switching state IZ9, such a pressure is applied in the first drive chamber 13 that a predetermined pressure p(IRR1) prevails in the first pump chamber 11. In switching state IZ10, the first outlet valve 16 is then opened, and so irrigation fluid can flow into the third subpath 83.

During switching states IZ5 to IZ10, the second outlet valve 26 is open, and so irrigation fluid under the pressure p(IRR1) flows into the fourth subpath 84. The opening of the first outlet valve 16 in switching state IZ10 is done at the moment when almost no more irrigation fluid is contained in the second pump chamber 21. This can be detected by the second sensor 29 via the position of the second elastic partition element 22.

Switching state IZ10 is only present for a brief period of 20 milliseconds for example. This is subsequently followed again by the first switching state IZ1, in which the second outlet valve 26 is closed.

Switching cycles IZ1 to IZ10 can be repeated until the irrigation fluid vessel 2 is empty.

Figure 3:
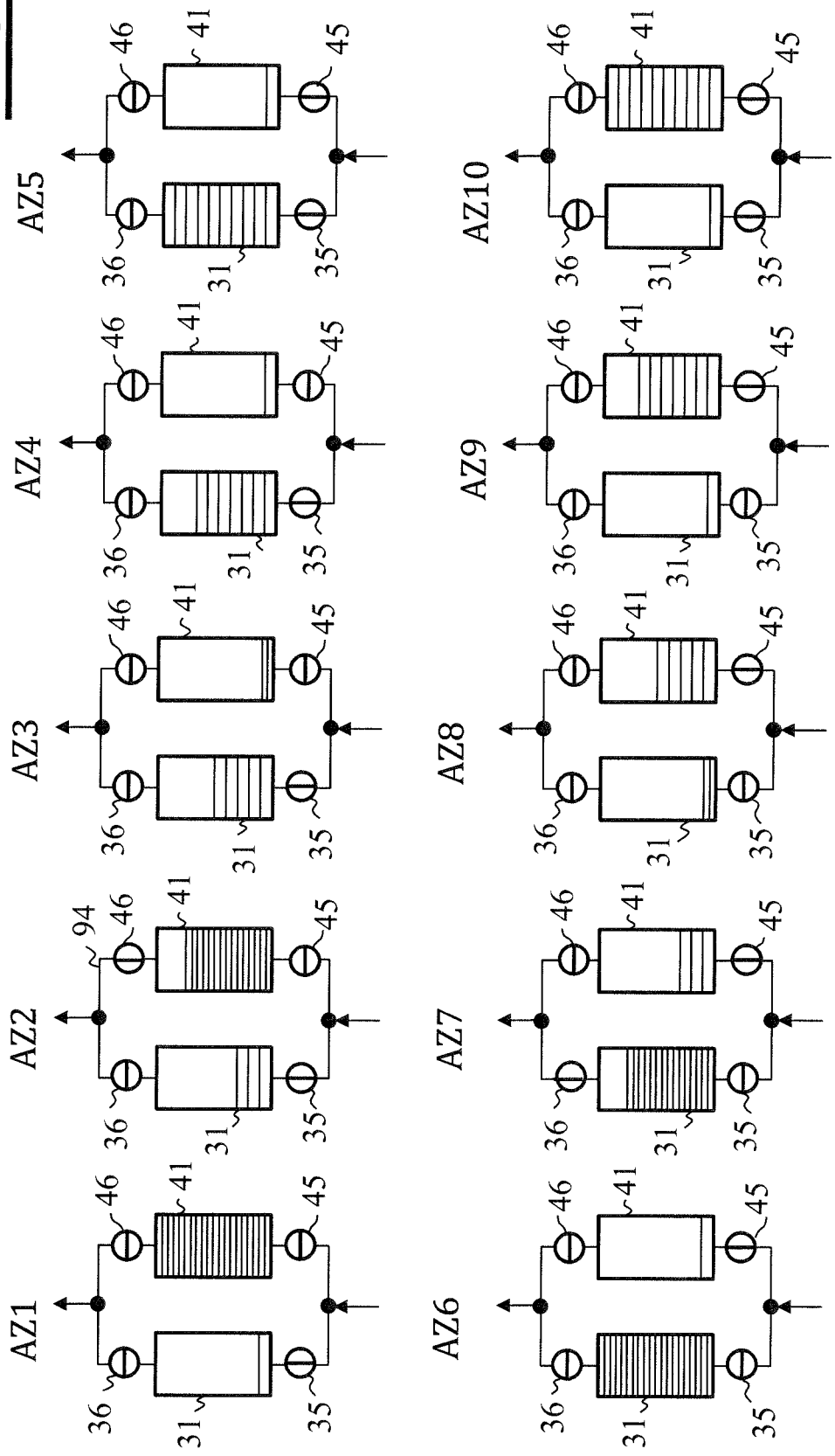
FIG. 3 shows a schematic representation of switching states of inlet and outlet valves of the third and fourth pump chamber of the system according to the invention; and, FIG. 4 shows schematic graphs of pressure profiles and volume flow profiles as a function of time in the system according to the invention.

FIG. 3 shows a schematic representation of switching states of the inlet valve 35 and of the outlet valve 36 of the third pump chamber 31 of the third fluid pump 30 and of switching states of the inlet valve 45 and of the associated outlet valve 46 of the fourth pump chamber 41 of the fourth fluid pump 40. The pump chambers 31 and 41 have both been filled with an aspiration fluid. The fill level with the aspiration fluid is indicated by the height of the uppermost shading line of the horizontal shading lines in the particular pump chamber. When the aspiration fluid in the particular pump chamber is contained under a low pressure, the distance between the horizontal shading lines in the particular pump chamber is relatively large. When the aspiration fluid in the particular pump chamber is contained under a high pressure, the distance between the horizontal shading lines in the particular pump chamber is relatively small.

In switching state AZ1, the third inlet valve 35 is open and the third outlet valve 36 is closed. A lower pressure is in the third drive chamber 33 than in the third pump chamber 31, and so aspiration fluid is sucked from the eye 6 to the surgical handpiece 5 and, from there, along the aspiration fluid flow path 9 into the third pump chamber 31. The fourth pump chamber 41 has been filled with aspiration fluid, with the fourth inlet valve 45 and the fourth outlet valve 46 being closed in switching state AZ1.

In the next switching state AZ2, the fourth outlet valve 46 is opened and a predetermined pressure is applied in the fourth drive chamber 43, and so aspiration fluid can flow out of the fourth pump chamber 43 through the fourth outlet valve 46 and, from there, into the subpath 94 up to the aspiration fluid collection vessel 50. At the same time, the third pump chamber 31 is increasingly filled with aspiration fluid. When the fourth pump chamber 41 is almost empty, the fourth outlet valve 46 is closed in the third switching state AZ3. The third pump chamber 31 is still filling with aspiration fluid or is almost filled therewith. Hardly any aspiration fluid is contained in the fourth pump chamber 41; see switching state AZ4. When the third pump chamber 31 has then been completely or almost completely filled with aspiration fluid, it being possible to determine this by the third sensor 39, the fourth inlet valve 45 is opened in the fifth switching state AZ5, and so aspiration fluid can flow not only along the subpath 91, but also along the subpath 92. This state of the third inlet valve 35 and the fourth inlet valve 45 being open at the same time and of aspiration fluid being sucked in under the predetermined pressure p(ASP1) is only present for a period of about 20 milliseconds. Subsequently, the third inlet valve 35 is closed in switching state AZ6, with the fourth inlet valve 45 continuing to remain open in order to suck in aspiration fluid. In the third pump chamber 31, a higher pressure is applied for the aspiration fluid situated therein.

In switching state AZ7, the third outlet valve 36 is opened in order to allow the aspiration fluid to flow out of the third pump chamber 31 into the subpath 93 and, from there, up to the aspiration fluid collection vessel 50. When the third pump chamber 31 is almost empty, the third outlet valve 36 is closed in switching state AZ8. The fourth pump chamber 41 is still filling with aspiration fluid; see switching state AZ9. In switching state AZ10, the third inlet valve 35 is opened, with the fourth inlet valve 45 still remaining open for a period of about 20 milliseconds. In the switching state AZ10, aspiration fluid is thus sucked in by the third pump chamber 31 and by the fourth pump chamber 41. This simultaneous sucking-in allows a transition to the subsequent switching state AZ1 without pulsation or pressure shock in the aspiration fluid flow path.

After switching state AZ10, switching state AZ1 follows again as described above.

FIG. 4 shows schematic graphs of pressure profiles and volume flow profiles as a function of time for the irrigation fluid flow path and the aspiration fluid flow path. Graph 200 shows the profile of a pressure in the irrigation fluid flow path. Graph 300 shows the profile of an intraocular pressure. Graph 400 shows the profile of a pressure in the aspiration fluid flow path. Graph 500 shows the profile of a volume flow in the irrigation fluid flow path. Graph 600 shows the profile of a volume flow in the aspiration fluid flow path. In the explanations which follow, the reference signs drawn in the graphs are specified in each case.

Initially, it is assumed that, for example, a steady pressure prevails in the first pump chamber 11 of the first fluid pump 10 (see 201), with no irrigation fluid flowing yet (see 501). The intraocular pressure has a constant resting value (see 301) and there is a positive pressure in the aspiration fluid flow path (see 401), and so nothing is being sucked in yet. In the aspiration fluid flow path, there is no volume flow yet (see 601).

At time T1, the outlet valve 16 is opened, with the drive chamber 13 building up a pressure with corresponding volume flow (see 202 and 502) until the irrigation fluid can flow out under the predetermined pressure p(IRR1) (see 203 and 503). The third inlet valve 35 is opened, and so aspiration fluid is sucked in by the third pump chamber 31 (see 602), whereupon the negative pressure rises in the aspiration fluid flow path (see 402) until a predetermined value p(ASP1) is reached (see 403), with a corresponding volume flow ensuing (see 603).

In the case of systems according to the prior art, in which the irrigation fluid is only provided by the hydrostatic pressure of an irrigation fluid vessel, the intraocular pressure drops with use of an aspiration suction-pressure (see in graph 300 the dashed line and 302 there). The pressure decreases by a value 303 which corresponds to the product from the hydraulic resistance of the irrigation hose line up to the eye and the volume flow in the irrigation line. However, in the case of the system according to the invention, the pressure in the irrigation fluid flow path is increased by this value at time T1 (see 202 and 203), and so the intraocular pressure remains unchanged during aspiration (see reference sign 304).

If a clogging (occlusion) due to a lens particle occurs in the aspiration fluid flow path, for example in a needle of the surgical instrument 5, the volume flow in the aspiration fluid flow path drops rapidly down to zero (see 604). In order to break up the occlusion, the negative pressure in the aspiration fluid flow path is increased (see 404), with the volume flow in the irrigation fluid flow path being lowered to zero (see 504).

In the case of systems according to the prior art, the intraocular pressure increases with the start of an occlusion and even briefly rises to a higher value than in the resting state (see 305), and this can be very hazardous for the patient. However, in the case of the system according to the invention, in a drive chamber of the first or second fluid pump that is active at this moment, such a pressure is predefined that, in the adjacent pump chamber, the pressure decreases inversely to the previously known profile as per 305 (see 204). The irrigation pressure therefore briefly drops below the hydrostatic pressure for a customary hanging of an irrigation fluid vessel and then reattains the hydrostatic pressure. What is achieved as a result is that the intraocular pressure remains constant even at the start of an occlusion (see 306).

During the subsequent presence of the occlusion, the volume flows in the irrigation fluid flow path and aspiration fluid flow path are unchanged at zero (see 505 and 605). When the occlusion then breaks up (see 405), aspiration fluid can flow into the aspiration fluid flow path again (see 606) and reach the third pump chamber 31 or the fourth pump chamber 41, this depending on whether it is the inlet valve 35 or the inlet valve 45 that is open. At this moment, the negative pressure in the now fillable pump chamber decreases, and so the differential pressure between the pump chamber and the drive chamber is reduced. This brings about a movement of the associated elastic partition element, which movement is detected by the associated sensor of the fluid pump. Subsequently, in the irrigation fluid flow path, the drive chamber of the fluid pump active at this moment is controlled such that the pressure in the irrigation fluid flow path rises according to a predefined profile (see 205 and with respect to the volume flow 506). This leads to no drop or only to a very slight drop in the intraocular pressure (see 307). The drop is considerably weaker than in the case of a system according to the prior art (see 308).

After this breakup of the occlusion, the driver chambers are controlled again as they were before the occlusion.

A method for switching of inlet valves and outlet valves for pump chambers of fluid pumps of the ophthalmosurgical system described above includes the steps of:

opening a first outlet valve 16 located in a direction of a flow downstream of an outlet of a first pump chamber 11 arranged adjacently of a first drive chamber 13 and separated therefrom by a first elastic partition element 12;

elastically deforming the first elastic partition element 12 so as to cause an irrigation fluid located inside of the first pump chamber 11 to flow in a third subpath 83 of an irrigation fluid flow path and, from there, to a surgical handpiece 5, wherein the irrigation fluid has a predetermined irrigation pressure;

opening a second inlet valve 25 located in a second subpath 82 of an irrigation fluid flow path in direction of flow upstream of an inlet of a second pump chamber 21 arranged adjacently of a second drive chamber 23 and separated therefrom by a second elastic partition element 22;

elastically deforming the second elastic partition element 22 so as to cause a negative pressure to develop in the second pump chamber 21 so as to cause irrigation fluid to flow from an irrigation fluid vessel 2 along the second subpath 82 and then into the second pump chamber 21;

closing the second inlet valve 25 and increasing the pressure in the second pump chamber 21 until an irrigation pressure occurs therein that is the predetermined irrigation pressure;

opening a second outlet valve 26 located in a fourth subpath 84 of an irrigation fluid flow path in a direction of a flow downstream of an outlet of the second pump chamber 21;

elastically deforming the second elastic partition element 22 so as to cause irrigation fluid to flow in the fourth subpath 84 of the irrigation fluid flow path, wherein both the first outlet valve 16 and the second outlet valve 26 are opened so as to permit, with the same predetermined irrigation pressure, irrigation fluid to flow from the third subpath 83 and the fourth subpath 84 to the surgical handpiece 5;

closing the first outlet valve 16;

opening a first inlet valve 15 located in a first subpath 91 of the irrigation fluid flow path in a direction of a flow upstream of an inlet of the first pump chamber 11;

elastically deforming the first elastic partition element 12 so as to cause irrigation fluid to flow in the first pump chamber 11;

closing the first inlet valve 15 and increasing the pressure in the first pump chamber 11 until the predetermined irrigation pressure occurs in the first pump chamber 11; and, closing the second outlet valve 26.

The following method steps are carried out in accordance with further features of the invention:

closing a third outlet valve 36 located in a direction of a flow downstream of an outlet of a third pump chamber 31 arranged adjacently of a third drive chamber 33 and mutually separated by a third elastic partition element 32;

opening a third inlet valve 35 located in a direction of a flow upstream of an inlet of the third pump chamber 31;

elastically deforming the third elastic partition element 32 so as to cause an aspiration fluid to flow from the surgical handpiece 5 along an aspiration fluid flow path into the third pump chamber 31, wherein the aspiration fluid is drawn by suction at a predetermined aspiration pressure;

opening a fourth outlet valve 46 located in a direction of a flow downstream of a fourth pump chamber 41 arranged adjacently of a fourth drive chamber 43 and separated therefrom by a fourth elastic partition element 42;

elastically deforming the fourth elastic partition element 42 so as to cause aspiration fluid that is contained inside of the fourth pump chamber 41 to flow through the fourth outlet valve 46 to an aspiration fluid collection container 50;

closing the fourth outlet valve 46;

opening a fourth inlet valve 45 located in a direction of a flow upstream of an inlet of the fourth pump chamber 41 with both the third inlet valve 35 and the fourth inlet valve 45 being open simultaneously so as to cause aspiration fluid to be drawn by suction through the third inlet valve 35 and the fourth inlet valve 45 at a predetermined aspiration pressure simultaneously;

closing the third inlet valve 35 and increasing the pressure in the third pump chamber 31 until an aspiration pressure occurs in the third pump chamber 31 that is the predetermined aspiration pressure;

opening the third outlet valve 36;

elastically deforming the third elastic partition element 32 so as to cause aspiration fluid to flow through the third outlet valve 36 to the aspiration fluid collection container 50; and, closing the fourth inlet valve 45.

It is understood that the foregoing description is that of the preferred embodiments of the invention and that various changes and modifications may be made thereto without departing from the spirit and scope of the invention as defined in the appended claims.

What is claimed is:

1. A method for switching of inlet valves and outlet valves for pump chambers of fluid pumps of an ophthalmosurgical system having an irrigation fluid flow path extending from an irrigation fluid source to a surgical instrument, the irrigation fluid flow path bifurcating upstream of the pump chambers into first and second subpaths and rejoining via third and fourth subpaths downstream of the pump chambers, the method comprising the steps of:

opening a first outlet valve located in a direction of a flow downstream of an outlet of a first pump chamber arranged adjacently of a first drive chamber and separated therefrom by a first elastic partition element;

elastically deforming the first elastic partition element so as to cause an irrigation fluid located inside of the first pump chamber to flow in the third subpath of the irrigation fluid flow path and, from there, to the surgical handpiece, wherein the irrigation fluid has a predetermined irrigation pressure;

opening a second inlet valve located in the second subpath of an irrigation fluid flow path in a direction of a flow upstream of an inlet of a second pump chamber arranged adjacently of a second drive chamber and separated therefrom by a second elastic partition element;

elastically deforming the second elastic partition element so as to cause a negative pressure to develop in the second pump chamber so as to cause the irrigation fluid to flow from the irrigation fluid source along the second subpath and then into the second pump chamber;

closing the second inlet valve and increasing a pressure in the second pump chamber until an irrigation pressure occurs therein that is the predetermined irrigation pressure;

opening a second outlet valve located in the fourth subpath of the irrigation fluid flow path in a direction of a flow downstream of an outlet of the second pump chamber;

elastically deforming the second elastic partition element so as to cause the irrigation fluid to flow in the fourth subpath of the irrigation fluid flow path, wherein both the first outlet valve and the second outlet valve are opened so as to permit, with the same predetermined irrigation pressure, the irrigation fluid to flow from the third subpath and the fourth subpath to the surgical handpiece;

closing the first outlet valve;

opening a first inlet valve located in the first subpath of the irrigation fluid flow path in a direction of a flow upstream of an inlet of the first pump chamber;

elastically deforming the first elastic partition element so as to cause the irrigation fluid to flow in the first pump chamber;

closing the first inlet valve and increasing a pressure in the first pump chamber until the predetermined irrigation pressure occurs in the first pump chamber; and, closing the second outlet valve.

2. The method of claim 1, comprising the further steps of:

closing a third outlet valve located in a direction of a flow downstream of an outlet of a third pump chamber arranged adjacently of a third drive chamber and mutually separated by a third elastic partition element;

opening a third inlet valve located in a direction of a flow upstream of an inlet of the third pump chamber;

elastically deforming the third elastic partition element so as to cause an aspiration fluid to flow from the surgical handpiece along an aspiration fluid flow path into the third pump chamber, wherein the aspiration fluid is drawn by suction at a predetermined aspiration pressure;

opening a fourth outlet valve located in a direction of a flow downstream of a fourth pump chamber arranged adjacently of a fourth drive chamber and separated therefrom by a fourth elastic partition element;

elastically deforming the fourth elastic partition element so as to cause aspiration fluid that is contained inside of the fourth pump chamber to flow through the fourth outlet valve to an aspiration fluid collection container;

closing the fourth outlet valve;

opening a fourth inlet valve located in a direction of a flow upstream of an inlet of the fourth pump chamber with both the third inlet valve and the fourth inlet valve being open simultaneously so as to cause the aspiration fluid to be drawn by suction through the third inlet valve and the fourth inlet valve at a predetermined aspiration pressure simultaneously;

closing the third inlet valve and increasing the pressure in the third pump chamber until an aspiration pressure occurs in the third pump chamber that is the predetermined aspiration pressure;

opening the third outlet valve;

elastically deforming the third elastic partition element so as to cause the aspiration fluid to flow through the third outlet valve to the aspiration fluid collection container; and, closing the fourth inlet valve.

* * * * *